United States Patent [19]

Kuhn

[11] Patent Number: 4,657,023

[45] Date of Patent: Apr. 14, 1987

[54] SELF-ADHERING ELECTRODE

[75] Inventor: Nicholas J. Kuhn, Edina, Minn.

[73] Assignee: Lec Tec Corporation, Eden Prairie, Minn.

[21] Appl. No.: 812,125

[22] Filed: Dec. 23, 1985

[51] Int. Cl.⁴ .......................... A61B 5/04; A61N 1/04
[52] U.S. Cl. ...................................... 128/640; 128/798
[58] Field of Search .................. 128/639–641, 128/644, 783, 798, 802, 803, 303.13

[56] References Cited

U.S. PATENT DOCUMENTS

| | | | |
|---|---|---|---|
| 2,047,308 | 7/1936 | Chapman | 128/798 |
| 4,166,465 | 9/1979 | Esty et al. | 128/798 X |
| 4,274,420 | 6/1981 | Hymes | 128/798 X |
| 4,422,461 | 12/1983 | Glumac | 128/802 |
| 4,522,211 | 6/1985 | Bare et al. | 128/640 |
| 4,539,996 | 9/1985 | Engel | 128/640 |

*Primary Examiner*—Lee S. Cohen
*Attorney, Agent, or Firm*—James V. Harmon

[57] ABSTRACT

An improved self-adhering electrode for application on the skin of the patient in which a portion of the electrically conductive layer forms an electrode that is substantially surrounded by a pressure-sensitive layer and the remainder of the conductive layer is covered by a substrate which is also conductive and sufficiently pliant to permit the electrode to adjust to the body contour.

10 Claims, 2 Drawing Figures

SELF-ADHERING ELECTRODE

BACKGROUND OF THE INVENTION

This invention relates to an improved, self-adhering monitoring and stimulation electrode in which a portion of an electrically conductive, e.g., metallic layer or film used to establish electrical contact with the skin is free to facilitate electrical contact with the desired apparatus. In this way, the sole conductive member is a uniform film or layer such as a metallic layer. In the prior art, contact between the electrode and the skin is made by a backing not necessarily electrically conductive which is connected to a snapping device for establishing contact with a wire that leads to the laboratory or testing equipment. Preferred electrodes of this type can be found in U.S. Pat. No. Re. 31,454 and U.S. Pat. No. 4,274,420.

An object of this invention is to provide an electrode for attachment to the skin, such as those used when the patient is connected to ECG measuring apparatus, in which an integral centrally located section of electrically conductive, e.g., metallic film functions to establish contact with the skin and with the electrical wire connected to test apparatus.

Another object of this invention is to provide an electrode that can be readily connected to the test equipment by means of the same "alligator" clips commonly used at this time to connect with the snaps of the prior electrodes. Another object of the invention is to provide an electrode which can be manufactured easier and less costly than prior art configurations.

A still further object of the invention is to provide an electrode which provides an area of breathability in the central portion of the electrode.

SUMMARY OF THE INVENTION

The objectives of this invention are accomplished in a medical electrode composed of an electrically conductive film or layer such as a metallic layer in which a portion of the metallic layer in the form of a "tab" is free to establish contact with a clamp or similar device that is connected to a wire leading to the testing apparatus. This metallic layer is substantially or totally surrounded and covered by a pressure-sensitive adhesive coated film except for the tab so as to establish good and uniform contact with the skin. The other side of the metallic layer is partially covered with a conductivity facilitating substrate.

DETAILED DESCRIPTION OF THE INVENTION

Medical electrodes are used in large numbers in increasing applications. The electrodes of this invention improve upon existing electrodes in a variety of ways.

Figure 1:
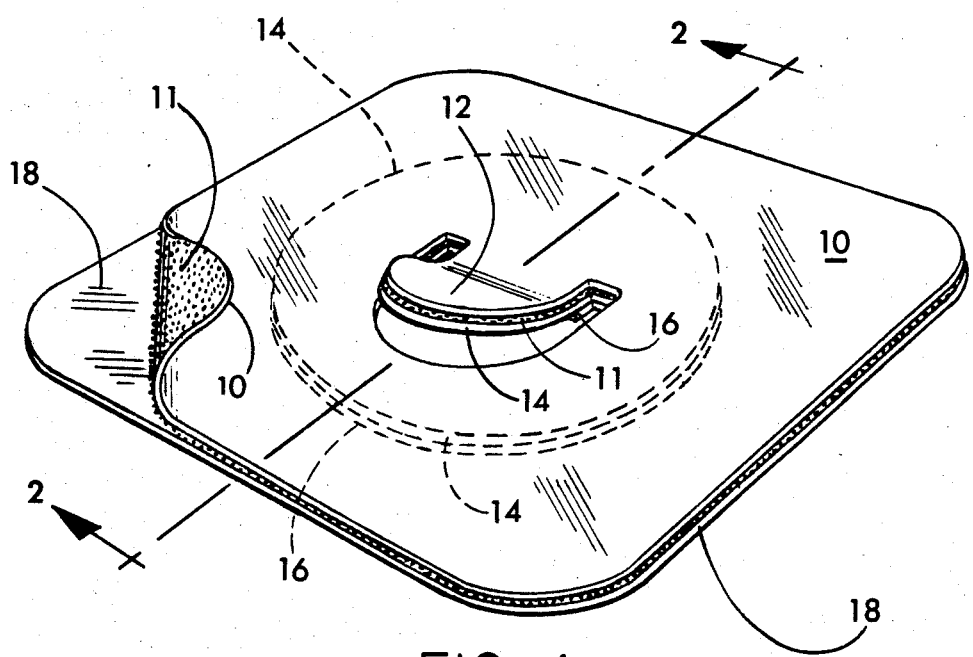
FIG. 1 is a perspective view of the preferred embodiment of the electrode.

FIG. 1 is a perspective view which shows the nonadhering surface of the pressure sensitive tape 10 which has been die-cut in the central portion to provide a U-shaped tab 12 in the central portion.

Figure 2:
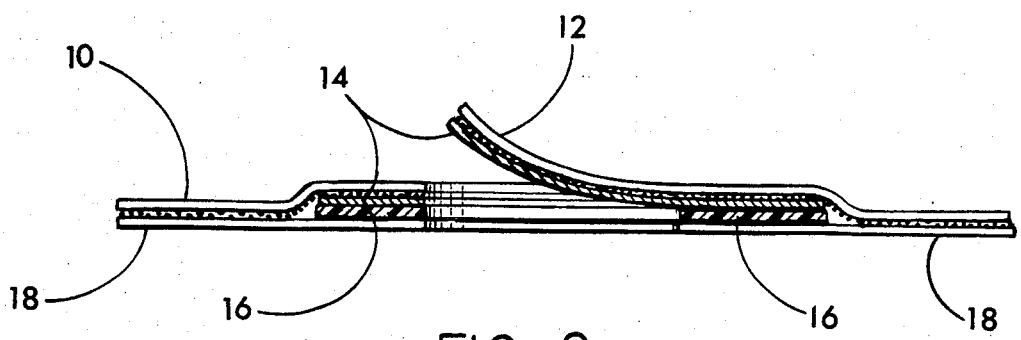
FIG. 2 is a cross-sectional view of the electrode along line 2—2 of FIG. 1.

The cross-sectional view seen in FIG. 2 shows the relative positioning of the pressure-sensitive adhesive tape 10, the conductive layer 14 which comprises, for example, a metal or metal alloy, the uniformly conductive flexible substrate 16, and the removable protective liner 18.

As set forth in the preferred embodiment of FIGS. 1 and 2, the pressure sensitive tape 10 is coextensive with the removable protective layer 18 and the flexible substrate 16 is coextensive with the uniformly conductive flexible metallic layer 14. The metallic layer 14 and substrate 16 are positioned concentrically within the larger pressure sensitive tape 10 such that the tape 10 extends beyond the edge of the metallic layer to provide a peripherally extending downwardly facing exposed pressure sensitive surface 11 to adhere to the skin. It is preferred, but not essential, that the surface 11 be a continuous border or ring surrounding the layers 14 and 16. In other embodiments, these layers may take a variety of shapes which provide a tab 12 centrally located for the technician to easily establish electrical contact on at least one side of the the metallic layer 14. Electrical contact with both sides of the metalic layer 14 may be accomplished by cutting out the tab 12 portion of pressure-sensitive tape 10 in the manner of cutting out the portion of the substrate 16 corresponding to tab 12. It will be noticed that the tab 12 provides a hole through which the skin may be seen thereby providing an area of breathability in the center of the electrode.

The pressure sensitive tape 10 may be any of a variety of tapes suitable and approved for contact with the skin. Illustrative of these tapes are acrylic based, solventless, hypoallergenic, pressure sensitive adhesive.

The flexible metallic film layer 14 is preferably tin, silver, gold, platinum, lead, aluminum, nickel or other suitable metal or alloy thereof or other conductive film known in the art.

Substrate 16 is composed of a uniformly electrically conductive flexible material in electrical contact with metallic layer 14 and capable of establishing electrical contact with the skin. Substrate 16 may or may not have adhesive properties. Illustative materials useful as substrates are conductive hydrophilic and hydrophobic resins derived from naturally occurring polysaccharides and synthetic resins. Karaya gum is preferred, but other gums or gels can be used. The substrate 16 is rendered electricallay conductive, e.g., by the addition of an electrolyte or other electrically conductive material such as silver paste or aluminum paste at a 1–5% level instead of electrolyte.

What is claimed is:

1. An electrode device for establishing electrical contact with the skin comprising,
    a flexible electrically conductive film layer, said film layer comprising a conductive sheet of predetermined area having a peripheral edge portion defining the perimeter of the film layer,
    an electrically conductive flexible substrate attached to a portion of one side of said film layer,
    a pressure sensitive adhesive coated film covering the other side of said conductive film layer and extending beyond the edge of said conductive film layer and said substrate to provide a surface for the pressure-sensitive adhesive coated film to adhere to the skin,
    a portion of the conductive film layer has a U-shaped tab forming a cut therein within the confines of the perimeter of the conductive film so that the tab is surrounded on all sides by the peripheral edge of the conductive film layer and said tab is also substantially surrounded by said substrate and by an exposed portion of said pressure-sensitive coated film, the U-shaped cut in the conductive film layer corresponds with the sides and end of the tab whereby the cut defines the edge of the tab, the surface of the tab adjacent the substrate being uncoated such that the tab provides an exposed electrically conductive surface for establishing electrical contact with the electrode, and a removable protective liner overlying the surface of said pressure-sensitive adhesive coated film, said substrate, and said tab.

2. The device of claim 1 in which the flexible film layer is a metallic film member selected from the group comprising aluminum, silver, gold, platinum, lead, nickel and tin.

3. The device of claim 1 in which the conductive substrate is sufficiently pliant to permit the electrode to adjust to the body contour of the patient and a portion of the substrate aligned with the tab having an opening therein beneath the tab, said substrate including karaya gum having an electrolyte dispersed therein.

4. The device of claim 3 wherein the conductive film layer is silver and the electrolyte is silver chloride.

5. The electrode of claim 1 wherein the tab is positioned out of vertical alignment with the substrate such that no substrate is positioned beneath the tab whereby the lower surface of the tab will not contact the substrate thereby enabling the tab to be more readily grasped and connected to test equipment.

6. The device of claim 1 wherein the adhesive coated film overlies the tab and includes a cut edge aligned with the U-shaped cut in the conductive film layer whereby the tab comprises a laminate composed of an overlying adhesive coated film and a conductive film layer of the same size and shape bonded thereto.

7. An improved self-adhering biomedical electrode for application on the skin of a patient comprising, an electrically conductive layer having a peripheral edge in which a portion of the electrically conductive layer forms an electrode, a U-shaped cut within the confines of the peripheral edge of the conductive layer to define a tab within the bounds of the electrically conductive layer having a free end and a connected end comprising a flexible electrical terminal enclosed and surrounded by the remainder of the conductive layer and comprising an integral portion thereof and the remainder of the conductive layer which surrounds the tab and is covered on one side by a substrate which is also conductive and sufficiently pliant to permit the electrode to adjust to the body contour of the patient and a portion of the substrate aligned with the tab having an opening therin beneath the tab whereby the tab will not become bonded to the substrate.

8. The biomedical electrode of claim 7 wherein the U-shaped cut defining said tab has a predetermined width for spacing the tab from the surrounding edges of said cut whereby the tab can be readily connected to test equipment.

9. An improved biomedical electrode for application on the skin of a patient comprising,
an electrically conductive layer comprising a conductive sheet of defined area having a peripheral edge portion defining the perimeter of the conductive layer,
the electrically conductive sheet has an arcuate shaped tab forming cut therein located within the perimeter of the conductive sheet and the arcuate shaped cut in the conductive sheet corresponds with the sides and end of the tab whereby the cut defines the edge of the tab formed in the conductive sheet within the perimeter of the conductive sheet, said tab having a free end and a connected end and comprising a flexible electrical terminal substantially surrounded by the remainder of the electrically conductive sheet,
an electrically conductive flexible substrate attached to one side of at least a portion of the remainder of the sheet and being sufficiently pliant to permit the electrode to adjust to the body contour of the patient and to form an electrical connection therewith,
a second layer of flexible sheet material applied to the other side of the electrically conductive sheet and being bonded thereto,
said second layer having an arcuate shaped cut therein corresponding in size and shape with the cut in the conductive layer and being aligned therewith whereby the tab is a laminate composed of two layers of equal size and shape and the electrically conductive layer of the tab is exposed to facilitate making electrical connections therewith.

10. The device of claim 9 wherein portions of the second layer extend peripherally beyond the perimeter of the electrically conductive layer, and an adhesive is provided on said portions to bond the electrode to the skin of the patient.

* * * * *